Feb. 23, 1960 L. R. HUTCHINSON Plant Pat. 1,916
APPLE TREE
Filed May 12, 1959
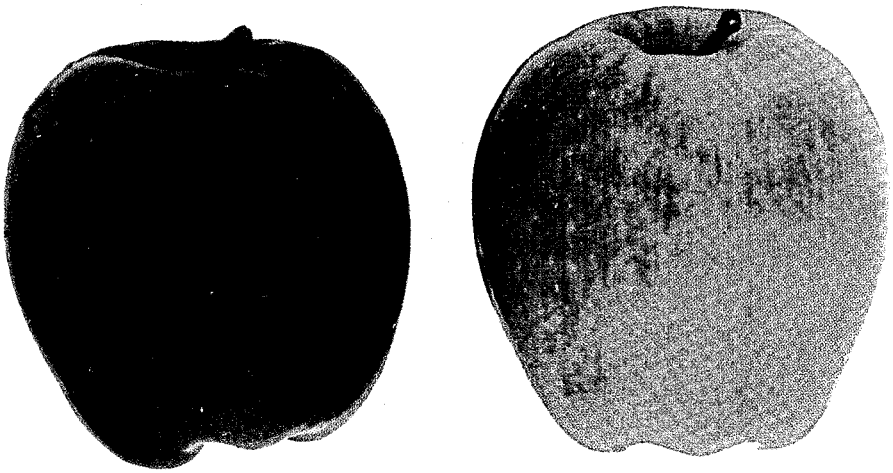
INVENTOR
Leonard R. Hutchinson
By Orville M. Kile
Plant Patent Agt.

United States Patent Office

Plant Pat. 1,916
Patented Feb. 23, 1960

1,916

APPLE TREE

Leonard R. Hutchinson, Tonasket, Wash., assignor to Columbia & Okanogan Nursery Co. Inc., Wenatchee, Wash.

Application May 12, 1959, Serial No. 812,785

1 Claim. (Cl. 47—62)

My present invention relates to an apple tree of the Delicious type, specifically with reference to early coloring of the fruit.

My new variety originated in my orchards in the State of Washington, as a bud sport of the variety Shotwell Delicious (Plant Patent No. 90), and has most of the qualities of its parent. The sporting limb of the original tree produces apples which are very similar to those of the remainder of the tree except that the fruit of the sporting limb has less pronounced striping in its final coloring, also starts coloring at a much earlier date and attains full color two or three weeks earlier than fruit on the rest of the tree.

I have asexually reproduced this new variety by means of budding, in my orchards at Tonasket, Washington. Second generation trees appear to be identical with the original sport and show the same characteristics of early coloring of their fruit and production of a much greater percentage of color on the fruit in the more shaded parts of the tree than does the Shotwell Delicious.

The accompanying illustrations show on the left a specimen of the fruit of my new variety, and on the right a specimen of the fruit of the parent variety. The photographs were taken about a month before maturity of my new variety and are in as true colors as the photographer could show by color photography. Both apples were picked on the same day and thus show the difference in coloring of the two varieties on a given date when the contrast is greatest. It should be noted, however, that as the two varieties reach maturity certain changes in coloring take place. The Shotwell Delicious will not only develop more color but the striping will be somewhat more prominent for a time until it reaches full coloring at which time the striping is again toned down by the overlaying color. The color changes in my new variety are described further in the specifications.

In the following detailed description of my new variety, color plate designations indicate Ridgway's Color Standards and Nomenclature, while other color names indicate the usual dictionary meaning of the terms.

*The tree*

Growth: Large; vigorous; spreading.
Production: Very productive of well-formed and well-colored fruit.
Hardiness: Has proved to be very hardy in Washington State.

*The fruit*

Size: Large.
Shape: Oblong conic to oblong blocky, varying somewhat according to local conditions where grown; slightly ribbed.
Cavity: Deep; broad; and frequently furrowed.
Stem: Medium in length and thickness.
Skin: Smooth; tenacious; medium thick; irregularly dotted with nearly-white dots or specks.
Core: Medium in size.
Flesh: Firm; tender; juicy; yellowish in color.
Flavor: Sub-acid.
Color: At about a month before maturity (as shown in illustrations) the color is approximately Oxblood Pl. I) and with no apparent stripings. As the color further develops it becomes much brighter and when the fruit is fully ripened the skin is dark red, between Carmine and Oxblood (Pl. I), with a few stripings of slightly lighter reds and occasional darker reds.
Seeds: Plump; brown; medium in size.

Although the apple most like my new variety is its parent, the variety is sometimes called similar to Royal Red Delicious (Plant Patent No. 1,278). This comparison is made because both varieties color rather early and are both of the Delicious type, but there is little other reason to say that they are similar. Coloring dates of my variety are only a little earlier than those of Royal Red Delicious, but the final color of my variety is a much darker red, and shows more stripes, instead of the overall cherry red blush of the Royal Red Delicious when it finishes coloring.

The Red King (Plant Patent No. 1,411) is sometimes mentioned as similar to my new variety but Red King has broad, variable but pronounced stripes whereas my new variety has narrow, rather uniform, obscure stripes. Red King originated as a sport of Starking Delicious whereas my new variety is a sport of Shotwell Red Delicious.

Having thus disclosed my discovery, I claim:

The new and distinct variety of apple tree of the Delicious type, characterized particularly by its similarity to its parent Shotwell Delicious (Plant Patent No. 90) except for the coloring of its fruits at a date two or three weeks earlier than the coloring of the fruits of its parent, and of a larger percentage of well-colored fruits.

References Cited in the file of this patent

UNITED STATES PATENTS

P.P. 1,278 Plough ..... May 18, 1954
P.P. 1,411 Brauns ..... Aug. 23, 1955